US00PP32300P2

(12) United States Plant Patent
Olesen

(10) Patent No.: US PP32,300 P2
(45) Date of Patent: Oct. 13, 2020

(54) COMPACT FLORIBUNDA ROSE PLANT NAMED 'POULCAS058'

(50) Latin Name: ***Rosa* hybrid**
Varietal Denomination: Poulcas058

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,250

(22) Filed: Sep. 4, 2019

(51) Int. Cl.
*A01H 5/02* (2018.01)
*A01H 6/74* (2018.01)

(52) U.S. Cl.
USPC ..... Plt./146
CPC ..... *A01H 6/749* (2018.05)

(58) Field of Classification Search
USPC ..... Plt./146
CPC ..... A01H 6/749; A01H 5/02
See application file for complete search history.

*Primary Examiner* — Keith O. Robinson

(57) ABSTRACT

A new garden rose plant of the Compact Floribunda class which has abundant, orange red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas058'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2008 and the resulting seeds were planted in a controlled environment in Fredensborg, Denmark. The new variety, named 'Poulcas058', originated as a single seedling from the stated cross.

The new variety may be distinguished from its male pollen parent and female seed parent primarily by the following characteristics. The male pollen parent plant has light red flowers while the new variety has orange red flowers. The female seed parent plant has light pink flowers while the new variety has orange red flowers.

The objective of the hybridization of this rose variety was to create a new and distinct variety with unique qualities, such as:

1. Uniform and abundant orange red flowers;
2. Vigorous, but compact growth when propagated on its own roots;
3. Exceptional disease resistance.

This combination of qualities is not present in previously available commercial cultivars of this type, known to the inventor, and distinguish 'Poulcas058' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulcas058' was selected in the spring of 2009 by the inventor as a single plant from the progeny of the aforementioned hybridization.

Asexual reproduction of 'Poulcas058' by rooted cuttings was first done by Mogens N. Olesen in the nursery in Fredensborg, Denmark in July, 2009. This initial and other subsequent asexual propagations conducted in controlled environments have demonstrated that the characteristics of 'Poulcas058' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas058'.

Specifically illustrated in FIG. 1 of the drawings are open flowers, flower buds upon opening on a branch, and petals detached revealing the receptacle and reproductive flower parts.

Figure 1:
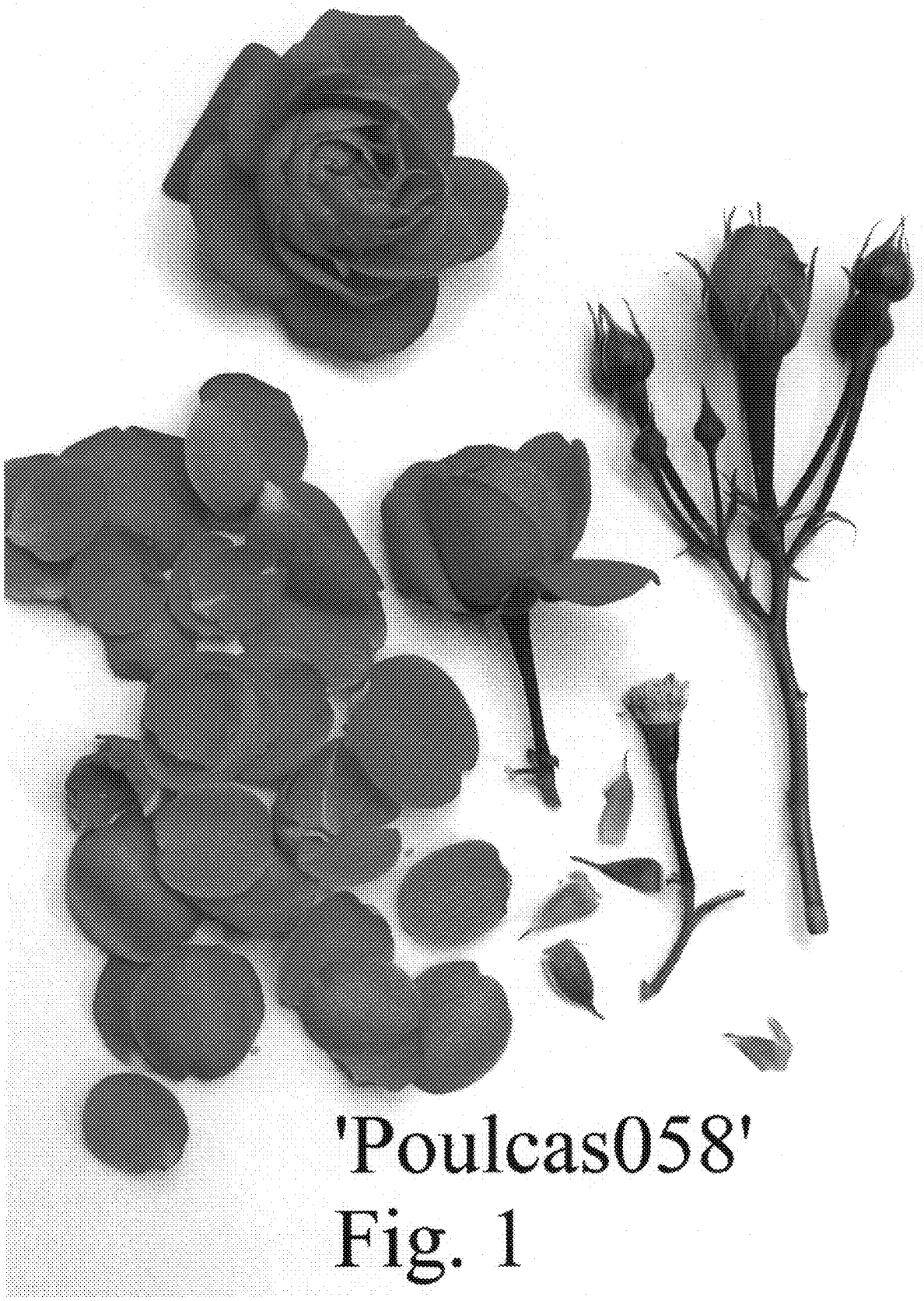
Figure 2:
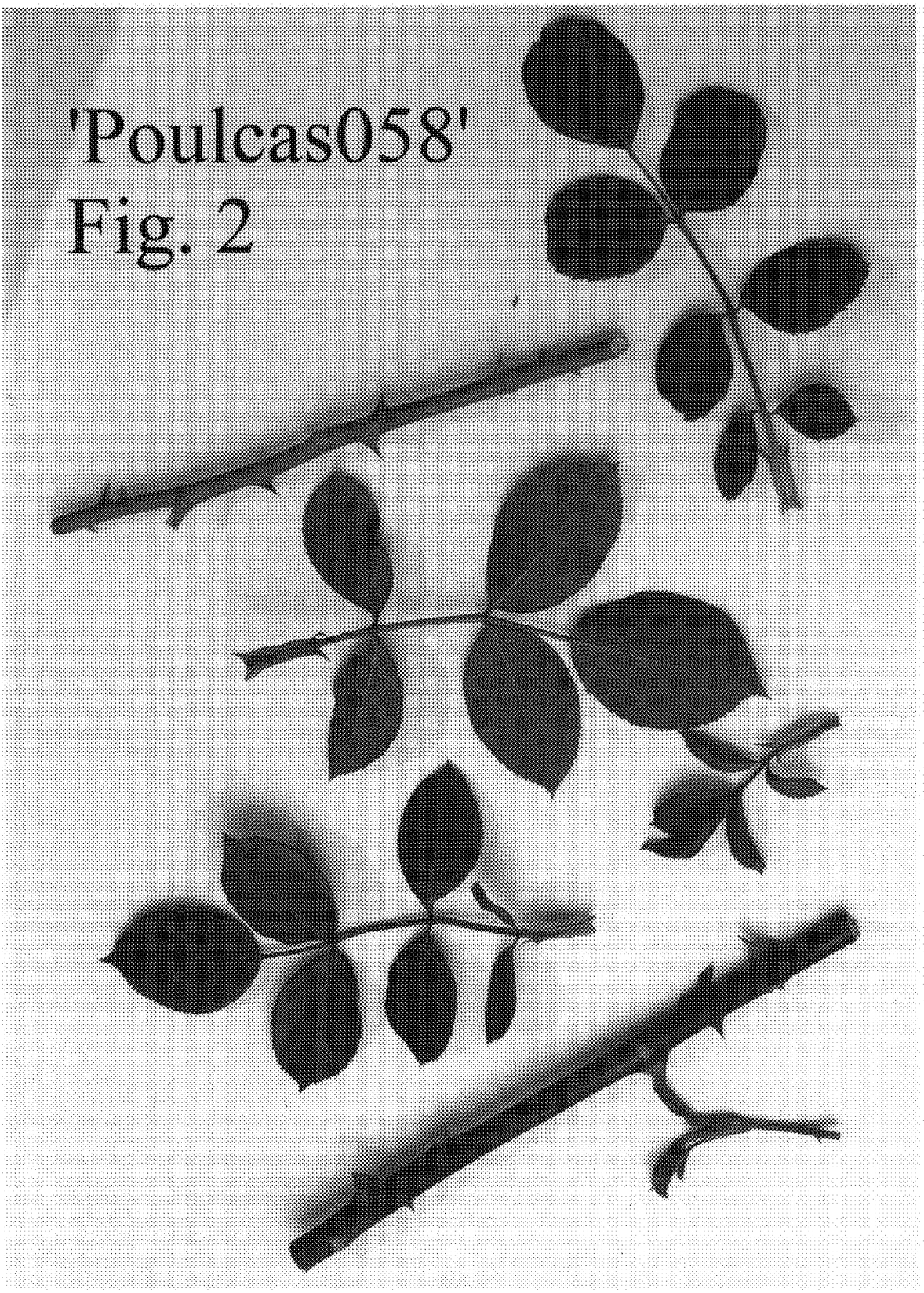

Specifically illustrated in FIG. 2 of the drawings are leaves and stems. Plants shown are 2 years of age.

DETAILED DESCRIPTION OF THE VARIETY

The following is a description of 'Poulcas058',as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas049', U.S. Plant Pat. No. 28,229 are compared to 'Poulcas058' in Chart 1.

CHART 1

| | 'Poulcas058' | 'Poulcas049' |
|---|---|---|
| Petal Count | 60 petals | 40 petals |
| Flower Diameter | 80 mm | 70 mm |
| General Tonality of Flower Color | Red Group 40A | Red Group 40A |

FLOWER AND FLOWER BUD

Blooming habit: Continuous.

Flower bud:

*Size*.—Upon opening, 24 mm in length from base of receptacle to end of bud. Bud diameter is 15 mm.

*Bud form*.—Globose.

*Bud color*.—As sepals divide petals are Orange-Red Group N34A.

*Sepal inner surface*.—Color: Yellow-Green Group 146D. Surface: Lightly pubescent.

*Sepal outer surface*.—Color: Yellow-Green Group 144A with intonations of Greyed-Orange Group 176A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—22 mm long, 9 mm wide.

*Receptacle*.—Texture: Smooth. Size: 5 mm in height, 6 mm wide. Color: Yellow-Green Group 144A with intonations of Greyed-Purple Group 183C and Greyed-Purple Group 187A. Shape: Funnel.

*Pedicel*.—Surface: Smooth. Length: 35 to 40 mm. Diameter: 2 or 3 mm. Color: Yellow-Green Group 144 a with very strong intonations of Greyed-Purple Group 183C. Strength: Strong.

*Peduncle*.—Length: 6 to 10 cm. Diameter: About 3 mm. Color: Yellow-Green Group 144A with intonations of Greyed-Purple Group 183C. Texture: Smooth.

Flower bud development: Flower buds are borne in clusters of 3 to 7 flower buds per stem.

Flower bloom:

*Fragrance*.—Moderate.

*Duration*.—The blooms have a duration on the plant of approximately 14 days. Petals fall cleanly away from plant after flowers have fully matured.

*Size*.—Flower diameter is 80 mm when open. Flower depth is 35 mm.

*Flower shape*.—Rosette, very double flower with many slightly overlapping petals of different sizes.

*Shape of flower, side view*.—The upper portion is flat, and the lower portion is flat concave.

Petalage: Under normal conditions, flowers have about 60 petals.

General tonality of flower: Open flowers are Red Group 40A.

Petal color:

*Upon opening, outer petals*.—Upper surface: Red Group 40A. Lower surface: At the basal zone, Red Group 51A, and Red Group 43B at the middle and marginal zone.

*Upon opening, inner petals*.—Upper surface: Red Group 40A. Lower surface: At the basal zone, Red Group 51A, and Red Group 43B at the middle and marginal zone.

*Basal petal spots, upon opening*.—Upper surface: Yellow Group 4D. Lower surface: Yellow Group 4D.

*After opening, outer petals*.—Upper surface: Red Group 40C. Lower surface: Red Group 43C.

*After opening, inner petals*.—Upper surface: Red Group 40C. Lower surface: Red Group 43C.

*Basal petal spots, after opening*.—Upper surface: Yellow Group 4D. Lower surface: Yellow Group 4D.

Petals:

*Petal reflex*.—Lightly reflexed.

*Margin*.—Entire and uniform. No undulations.

*Shape*.—Broad and elliptic. Apex shape: Rounded. Base shape: Round.

*Size*.—About 38 mm (l)×35 mm (w).

*Texture*.—Smooth.

*Thickness*.—Average.

Petaloids:

*Size*.—10 mm (l) by 15 mm (w).

*Quantity*.—About 5.

*Shape*.—Generally rounded, with a rounded base and apex.

*Color*.—Red Group 40A on the upper surface. The lower surface is Red Group 43B. At the petaloid base, Yellow Group 4D on upper and lower surface.

*Margins*.—Strong undulation.

Reproductive flower parts:

*Pollen*.—None observed.

*Anthers*.—Size: 2 mm in length. Color: Yellow Group 11C. Quantity: 45 on average.

*Filaments*.—Color: Yellow Group 9B with intonations of Red Group 43C. Length: 5 mm.

*Pistils*.—Length: 6 mm. Quantity: 26 on average.

*Stigmas*.—Color: Yellow-White Group 158A.

*Styles*.—Color: Yellow-White Group 158A.

*Location of stigmas*.—Inferior in location relative to the length of the filaments and the height of the anthers.

*Hips*.—None Observed.

PLANT

Plant growth: Upright, bushy. Plants are about 75 cm in height, and 65 cm wide.

Stems:

*Color of juvenile growth*.—Yellow-Green Group 144B with intonations of Greyed-Orange Group 166A.

*Color of mature growth*.—Yellow-Green Group 144A.

*Length*.—Canes are about 35 cm from the base of the plant to the flowering portion.

*Diameter*.—About 6 to 8 mm.

*Internodes*.—On mature canes about 45 mm between nodes.

*Surface texture*.—Young wood: Smooth. Older wood: Smooth.

Long prickles:

*Incidence*.—3 prickles per 10 cm of stem.

*Size*.—Average length of prickles on mature stems is 8 mm.

*Shape*.—Upper portion is linear. Lower portion is concave.

*Color*.—Juvenile prickles: Greyed-Orange Group 166B and Yellow-Green Group 144A. Mature prickles: Greyed-Orange Group 164A, 164B.

Plant foliage:

*Compound leaf*.—140 mm (l)×95 (w).

*Quantity*.—2 leaves per 10 cm of stem on average.

*Color of juvenile foliage*.—Upper side: Yellow-Green Group 144A with intonations of Greyed-Purple Group 183B. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 25 mm long, 4 mm wide. Quantity: 2 per compound leaf. Shape: Linear, slightly broad based with outward extending apices. Margins: Finely serrated. Color: Yellow-Green Group 144A.

*Petiole*.—Length: About 35 mm. Diameter: 2 mm. Upper surface color: Yellow-Green Group 144A with light intonations of Greyed-Red Group 181D. Lower surface color: Yellow-Green Group 144A.

*Rachis*.—Length: About 50 mm. Upper surface color: Yellow-Green Group 144A. Lower surface color: Yellow-Green Group 144A.

*Leaflet*.—Quantity: 5 to 7 leaflets. Margins: Serrated. Size: Terminal leaflets are about 53 mm long, 38 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulcas058', substantially as illustrated and described herein, due to its abundant orange red flowers, disease resistance, and extended period of bloom.

* * * * *

'Poulcas058'